(12) United States Patent
Carstens

(10) Patent No.: US 9,850,525 B2
(45) Date of Patent: Dec. 26, 2017

(54) CAS9-BASED ISOTHERMAL METHOD OF DETECTION OF SPECIFIC DNA SEQUENCE

(71) Applicant: Agilent Technologies, Inc., Loveland, CO (US)

(72) Inventor: Carsten-Peter Carstens, La Jolla, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 144 days.

(21) Appl. No.: 14/607,781

(22) Filed: Jan. 28, 2015

(65) Prior Publication Data

US 2015/0211058 A1 Jul. 30, 2015

Related U.S. Application Data

(60) Provisional application No. 61/932,839, filed on Jan. 29, 2014.

(51) Int. Cl.
*C12Q 1/68* (2006.01)
*C12Q 1/70* (2006.01)
*C12N 15/63* (2006.01)

(52) U.S. Cl.
CPC .......... *C12Q 1/6844* (2013.01); *C12N 15/63* (2013.01); *C12Q 1/70* (2013.01)

(58) Field of Classification Search
CPC .......... C12Q 1/6844; C12Q 1/70; C12N 15/63
See application file for complete search history.

(56) References Cited

U.S. PATENT DOCUMENTS

| 7,189,508 | B2 | 3/2007 | Sorge et al. |
| 8,697,359 | B1 * | 4/2014 | Zhang .................... C12N 15/85 424/94.1 |
| 2007/0054301 | A1 | 3/2007 | Becker et al. |
| 2012/0196330 | A1 | 8/2012 | Nelson et al. |
| 2013/0281307 | A1 | 10/2013 | Li et al. |
| 2013/0323795 | A1 | 12/2013 | Duthie et al. |
| 2013/0330777 | A1 | 12/2013 | Zhang et al. |

FOREIGN PATENT DOCUMENTS

| WO | WO 2013/176772 | * 11/2013 | ............. C07K 19/00 |
| WO | 2013188037 A2 | 12/2013 | |

OTHER PUBLICATIONS

Li et al., A new class of homogeneous nucleic acid probes based on specific displacement hybridization, Nucleic Acids Research, 2002, vol. 30, No. 2 e5.*
Esvelt, Kevin M. et al., Orthogonal Cas9 proteins for RNA guided gene regulation and editing, Nature Methods, vol. 10, No. 11, pp. 1116-1121, 2013.
Mali, Prashant et al., RNA-Guided Human Genome Engineering via Cas9, Science, vol. 339, No. 6121, pp. 823-826, 2013.
NCBI, reference sequence, Reference sequence WP_01440754.1, May 18, 2013.
Ran, Ann F., et al., Double Nicking by RNA-Guided CRISPR Cas9 for Enhanced Genome Editing Specificity, Cell, vol. 154, No. 6, pp. 1380-1389, 2013.

(Continued)

*Primary Examiner* — Reza Ghafoorian

(57) ABSTRACT

The present invention relates to an isothermal method for detecting in a sample a target nucleic acid strand.

16 Claims, 2 Drawing Sheets

(56) References Cited

OTHER PUBLICATIONS

Ran, Ann F., et al., Genome engineering using the CRISPRCas9 system, Nature Protocols, vol. 8, No. 11, pp. 2281-2308, 2013.
International Search Report, PCT/US2015/013299, dated Dec. 28, 2015.
Written Opinion, PCT/US2015/013299, dated Apr. 16, 2015.
Notomi et al., "Loop-mediated isothermal amplification of DNA," Nucleic Acids Research (2000): 28(12): e63:i-vii.
Gill et al., "Nucleic Acid Isothermal Amplification Technologies—A Review," Nucleosides, Nucleotides, and Nucleic Acids (2008): 27:224-243.
Gasiunas et al., "Cas9-crRNA ribonucleoprotein complex mediates specific DNA cleavage for adaptive immunity in bacteria," PNAS (published onlines Sep. 4, 2012): E2579-E2586.
Jinek et al, "A Programmable Dual-RNA-Guided DNA Endonuclease in Adaptive Bacterial Immunity," Science (2012): 337:816-821.

* cited by examiner

SEQUENCE LISTING

<160> NUMBER OF SEQ ID NOS: 3

<210> SEQ ID NO 1
<211> LENGTH: 1367

<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400
```

```
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
        450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
        530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Ala Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
        610                 615                 620
Leu Phe Glu Asp Arg Gly Met Ile Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
        690                 695                 700
Lys Glu Asp Ile Gln Lys Ala Gln Val Ser Gly Gln Gly His Ser Leu
705                 710                 715                 720
His Glu Gln Ile Ala Asn Leu Ala Gly Ser Pro Ala Ile Lys Lys Gly
                725                 730                 735
Ile Leu Gln Thr Val Lys Ile Val Asp Glu Leu Val Lys Val Met Gly
            740                 745                 750
His Lys Pro Glu Asn Ile Val Ile Glu Met Ala Arg Glu Asn Gln Thr
        755                 760                 765
Thr Gln Lys Gly Gln Lys Asn Ser Arg Glu Arg Met Lys Arg Ile Glu
    770                 775                 780
Glu Gly Ile Lys Glu Leu Gly Ser Gln Ile Leu Lys Glu His Pro Val
785                 790                 795                 800
Glu Asn Thr Gln Leu Gln Asn Glu Lys Leu Tyr Leu Tyr Tyr Leu Gln
                805                 810                 815
```

-continued

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
    835                 840                 845

Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn

```
                    1220                1225               1230

Phe Leu Tyr Leu Ala Ser His Tyr Glu Lys Leu Lys Gly Ser Pro
        1235                1240               1245

Glu Asp Asn Glu Gln Lys Gln Leu Phe Val Glu Gln His Lys His
        1250                1255               1260

Tyr Leu Asp Glu Ile Ile Glu Gln Ile Ser Glu Phe Ser Lys Arg
        1265                1270               1275

Val Ile Leu Ala Asp Ala Asn Leu Asp Lys Val Leu Ser Ala Tyr
        1280                1285               1290

Asn Lys His Arg Asp Lys Pro Ile Arg Glu Gln Ala Glu Asn Ile
        1295                1300               1305

Ile His Leu Phe Thr Leu Thr Asn Leu Gly Ala Pro Ala Ala Phe
        1310                1315               1320

Lys Tyr Phe Asp Thr Thr Ile Asp Arg Lys Arg Tyr Thr Ser Thr
        1325                1330               1335

Lys Glu Val Leu Asp Ala Thr Leu Ile His Gln Ser Ile Thr Gly
        1340                1345               1350

Leu Tyr Glu Thr Arg Ile Asp Leu Ser Gln Leu Gly Gly Asp
        1355                1360               1365

<210> SEQ ID NO 2
<211> LENGTH: 1367
<212> TYPE: PRT
<213> ORGANISM: Artificial Sequence
<220> FEATURE:
<223> OTHER INFORMATION: MUTANT

<400> SEQUENCE: 2

Met Asp Lys Lys Tyr Ser Ile Gly Leu Ala Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
```

```
            210                 215                 220
Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Ala Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
            610                 615                 620

Leu Phe Glu Asp Arg Gly Met Ile Glu Glu Arg Leu Lys Thr Tyr Ala
625                 630                 635                 640
```

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
                740                 745                 750

His Lys Pro Glu Asn Ile Val Ile Glu Met Ala Arg Glu Asn Gln Thr
                755                 760                 765

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Ile Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
        1010                1015                1020

Ser Glu Gln Glu Ile Gly Lys Ala Thr Ala Lys Tyr Phe Phe Tyr
        1025                1030                1035

Ser Asn Ile Met Asn Phe Phe Lys Thr Glu Ile Thr Leu Ala Asn
        1040                1045                1050

```
Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 3
<211> LENGTH: 1367
<212> TYPE: PRT
<213> ORGANISM: Artificial Sequence
<220> FEATURE:
<223> OTHER INFORMATION: MUTANT

<400> SEQUENCE: 3

Met Asp Lys Lys Tyr Ser Ile Gly Leu Asp Ile Gly Thr Asn Ser
1               5                   10                  15

Gly Trp Ala Val Ile Thr Asp Asp Tyr Lys Val Pro Ser Lys Lys Phe
            20                  25                  30
```

-continued

```
Lys Val Leu Gly Asn Thr Asp Arg His Ser Ile Lys Lys Asn Leu Ile
         35                  40                  45
Gly Ala Leu Leu Phe Gly Ser Gly Glu Thr Ala Glu Ala Thr Arg Leu
 50                  55                  60
Lys Arg Thr Ala Arg Arg Tyr Thr Arg Arg Lys Asn Arg Ile Cys
 65                  70                  75              80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Ala Asp
130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Ile Tyr
            180                 185                 190
Asn Gln Leu Phe Glu Glu Asn Pro Ile Asn Ala Ser Arg Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Arg Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Ser Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
```

```
                450             455             460
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Ala Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Gly Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
                740                 745                 750

His Lys Pro Glu Asn Ile Val Ile Glu Met Ala Arg Glu Asn Gln Thr
                755                 760                 765

Thr Gln Lys Gly Gln Lys Asn Ser Arg Glu Arg Met Lys Arg Ile Glu
                770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
                820                 825                 830

Ser Asp Tyr Asp Val Asp Ala Ile Val Pro Gln Ser Phe Ile Lys Asp
                835                 840                 845

Asp Ser Ile Asp Asn Lys Val Leu Thr Arg Ser Asp Lys Asn Arg Gly
                850                 855                 860

Lys Ser Asp Asn Val Pro Ser Glu Glu Val Val Lys Lys Met Lys Asn
865                 870                 875                 880
```

-continued

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
            1010                1015                1020

Ser Glu Gln Glu Ile Gly Lys Ala Thr Ala Lys Tyr Phe Phe Tyr
            1025                1030                1035

Ser Asn Ile Met Asn Phe Phe Lys Thr Glu Ile Thr Leu Ala Asn
            1040                1045                1050

Gly Glu Ile Arg Lys Arg Pro Leu Ile Glu Thr Asn Gly Glu Thr
            1055                1060                1065

Gly Glu Ile Val Trp Asp Lys Gly Arg Asp Phe Ala Thr Val Arg
            1070                1075                1080

Lys Val Leu Ser Met Pro Gln Val Asn Ile Val Lys Lys Thr Glu
            1085                1090                1095

Val Gln Thr Gly Gly Phe Ser Lys Glu Ser Ile Leu Pro Lys Arg
            1100                1105                1110

Asn Ser Asp Lys Leu Ile Ala Arg Lys Lys Asp Trp Asp Pro Lys
            1115                1120                1125

Lys Tyr Gly Gly Phe Asp Ser Pro Thr Val Ala Tyr Ser Val Leu
            1130                1135                1140

Val Val Ala Lys Val Glu Lys Gly Lys Ser Lys Lys Leu Lys Ser
            1145                1150                1155

Val Lys Glu Leu Leu Gly Ile Thr Ile Met Glu Arg Ser Ser Phe
            1160                1165                1170

Glu Lys Asn Pro Ile Asp Phe Leu Glu Ala Lys Gly Tyr Lys Glu
            1175                1180                1185

Val Lys Lys Asp Leu Ile Ile Lys Leu Pro Lys Tyr Ser Leu Phe
            1190                1195                1200

Glu Leu Glu Asn Gly Arg Lys Arg Met Leu Ala Ser Ala Gly Glu
            1205                1210                1215

Leu Gln Lys Gly Asn Glu Leu Ala Leu Pro Ser Lys Tyr Val Asn
            1220                1225                1230

Phe Leu Tyr Leu Ala Ser His Tyr Glu Lys Leu Lys Gly Ser Pro
            1235                1240                1245

Glu Asp Asn Glu Gln Lys Gln Leu Phe Val Glu Gln His Lys His
            1250                1255                1260

Tyr Leu Asp Glu Ile Ile Glu Gln Ile Ser Glu Phe Ser Lys Arg
            1265                1270                1275

-continued

```
Val Ile Leu Ala Asp Ala Asn Leu Asp Lys Val Leu Ser Ala Tyr
    1280            1285                1290

Asn Lys His Arg Asp Lys Pro Ile Arg Glu Gln Ala Glu Asn Ile
    1295            1300                1305

Ile His Leu Phe Thr Leu Thr Asn Leu Gly Ala Pro Ala Ala Phe
    1310            1315                1320

Lys Tyr Phe Asp Thr Thr Ile Asp Arg Lys Arg Tyr Thr Ser Thr
    1325            1330                1335

Lys Glu Val Leu Asp Ala Thr Leu Ile His Gln Ser Ile Thr Gly
    1340            1345                1350

Leu Tyr Glu Thr Arg Ile Asp Leu Ser Gln Leu Gly Gly Asp
    1355            1360                1365
```

CAS9-BASED ISOTHERMAL METHOD OF DETECTION OF SPECIFIC DNA SEQUENCE

CROSS REFERENCE TO RELATED APPLICATION

This application claims priority to U.S. Provisional Application No. 61/932,839 filed on Jan. 29, 2014. The content of the application is incorporated herein by reference in its entirety.

FIELD OF THE INVENTION

The present invention relates to the field of molecular biology. More specifically, it relates to methods for detecting specific DNA sequence using a CRISPR/CAS system.

BACKGROUND OF THE INVENTION

Detection of nucleic acid sequences (e.g., DNA sequences) is widely used in the fields of molecular biology and diagnosis for detection and identification of infectious diseases, genetic disorders and other research purposes. For detecting and analyzing a small quantity of nucleic acids, nucleic acid amplification technologies are used. Among them, the polymerase chain reaction (PCR) is the most widely used method.

While a very powerful technique, PCR has certain limitations as it requires multiple reiterative thermal cycles among different temperatures for different stages, e.g., denaturing, extension, and re-annealing respectively. Since each stage must be sufficiently long, the entire PCR reaction is very time consuming. To address this issue, the time duration for each stage can be limited. Yet, during the reiterative thermal cycling, a target sequence is extended and amplified efficiently only at the extension stage. As a result, PCR is limited in the size of the sequence to be amplified and the efficient amplification range is generally below 2000 bp. Furthermore, relying on precise cycling of a reaction cocktail between different temperatures, PCR requires expensive equipment such as a thermocycler. In addition, the repeated denaturing stage exposes the reaction cocktail to a temperature as high as 90° C. or above. Such a high temperature can damage some components of the cocktail and thereby negatively impact the length and quality of the amplified products. Thus, although there are more than 50 different PCR techniques in use, PCR-based detection methods remain expensive, time-consuming, instrument and reagent-intensive, and require extensive sample preparation.

An alternative to PCR is isothermal amplification. This alternative technology does not rely on reiterative cycles among different temperatures to achieve amplification and is therefore referred to as isothermal amplification. Several isothermal amplification techniques are known in the art. In general, isothermal amplification systems provide the advantages of speed, ease of use, the ability to utilize highly processive DNA polymerases, and do not require expensive thermocyclers. Yet, one of the limitations of isothermal amplification schemes is the relatively low specificity due to annealing of primers at temperatures lower (e.g., 37° C. or lower) as compared to those used in PCR. Thus, there is a need for highly specific isothermal amplification methods.

The CRISPR/CAS system is a class of nucleic acid targeting system originally discovered in prokaryotes that somewhat resemble siRNA/miRNA systems found in eukaryotes. The system consists of an array of short repeats with intervening variable sequences of constant length (i.e., clusters of regularly interspaced short palindromic repeats, or CRISPRs) and CRISPR-associated (CAS) proteins.

In CRISPR, each repetition contains a series of base pairs followed by the same or a similar series in reverse and then by 30 or so base pairs known as "spacer DNA." The spacers are short segments of DNA from a virus, which have been removed from the virus or plasmid and incorporated into the host genome between the short repeat sequences, and serve as a "memory" of past exposures. The RNA of the transcribed CRISPR arrays is processed by a subset of the CAS proteins into small guide RNAs containing the viral or plasmid sequences, which direct CAS-mediated cleavage of viral or plasmid nucleic acid sequences that contain so-called protospacer adjacent motif (PAM) site and correspond to the small guide RNAs. That is, the CRISPR/CAS system functions as a prokaryotic immune system, as the spacers recognize and silence exogenous genetic elements in a manner analogous to RNAi in eukaryotic organisms thereby conferring resistance to exogenous genetic elements such as plasmids and phages.

SUMMARY OF INVENTION

This invention relates to novel isothermal amplification methods that provide specificity higher than conventional isothermal amplification methods. The novel isothermal amplification methods overcome the limitation of conventional methods by utilizing the CRISPR/CAS system.

Accordingly, in one aspect, the invention provides an isothermal method for detecting in a sample a target nucleic acid strand. The method takes advantages of the CRISPR/CAS system and uses related nuclease (such as CAS9) and guide RNAs to target two separate sequences in the target nucleic acid strand. To that end, any target nucleic acid strand of interest can be detected using the method as long as it has, from 5' to 3', two separate targetable sites: (i) a first CAS-targeted site (or a 5' CAS targeted site) having a first target sequence and a first protospacer adjacent motif (PAM) site and (ii) a second CAS-targeted site (or a 3' CAS targeted site) having a second target sequence and a second PAM site. The first target sequence is different from the second target sequence.

In some embodiments (such as that shown in FIGS. 1 and 2), the first PAM site and the second PAM site are 3' to the first target sequence and the second target sequence, respectively. The method includes the following steps.

First, one can contact a sample suspected to contain the target nucleic acid strand with: a first CAS9 mutant having a single-strand nicking activity, a first guide RNA (gRNA) targeting the first/5' CAS-targeted site, a strand-displacing nucleic acid polymerase, and nucleotides. This contacting step is carried out under conditions allowing the following two reactions: (1) nicking of the target nucleic acid strand by the CAS9 mutant at the first/5' CAS targeted cite), and (2) strand-displacing by the strand-displacing nucleic acid polymerase to create one or more copies of a section of the target nucleic acid strand. Each copy contains the sequence of the second/3' CAS-targeted site.

Second, one can contact the one or more copies with: a second CAS9 mutant having a single-strand nicking activity, a second gRNA targeting the second CAS-targeted site, a strand-displacing nucleic acid polymerase, nucleotides, and one or more circular probes or templates. Each of the circular probes/templates has a CAS region that is complementary to the second CAS-targeted site and a tag region. This contacting step is carried out under conditions allowing the following three reactions: (1) hybridizing of the one or more copies to the one or more circular probes to generate one or more annealed copies, (2) nicking of these one or more annealed copies by the second CAS9 mutant at the second CAS-targeted cite, and (3) strand-displacing by the strand-displacing nucleic acid polymerase to create one or more extension products of the one or more annealed copies. Each product contains a detecting region that is complementary to the tag region and is recognizable by a detecting agent Third, once the extension products are generated, one can detect presence of the one or more extension products using various suitable means, such as the detecting agent. The presence of the one or more extension products is an indicator of the presence of the target nucleic acid strand in the sample.

The above-mentioned two contacting steps can be carried out sequentially or simultaneously. For this latter case, the invention provides a detection method, which includes the following steps.

One can first prepare a reaction mixture containing (i) a sample suspected to contain the target nucleic acid strand, (ii) a first CAS9 mutant having a single-strand nicking activity, (iii) a first gRNA targeting the first CAS-targeted site, (iv) a second CAS9 mutant having a single-strand nicking activity, (v) a second gRNA targeting the second CAS-targeted site, (vi) a strand-displacing nucleic acid polymerase, (vii) nucleotides, and (viii) one or more circular probes or templates. Each of the circular probes/templates has a CAS region that is complementary to the second CAS-targeted site and a tag region.

Then, the reaction mixture is incubated under conditions permitting the following five reactions: (i) nicking the target nucleic acid strand by the first CAS9 mutant at the first CAS targeted cite (e.g., at a site between the first target sequence and the first PAM site the, and 5' to the first PAM site), (ii) strand displacing by the strand-displacing nucleic acid polymerase to create one or more copies of a section of the target nucleic acid strand, each copy containing the second CAS-targeted site. (iii) hybridizing the one or more copies to the one or more circular probes to generate one or more annealed copies, (iv) nicking the one or more annealed copies by the second CAS9 mutant at the second CAS-targeted cite (e.g., at a site between the second target sequence and the second PAM site the, and 5' to the second PAM site), and (v) strand displacing by the strand-displacing nucleic acid polymerase to create one or more extension products of the one or more annealed copies. Each product contains a detecting region that is complementary to the tag region and recognizable by a detecting agent.

Again, once the extension products are generated, one can detect presence of the one or more extension products using the detecting agent. The presence of the one or more extension products is an indicator of the presence of the target nucleic acid strand in the sample.

In the above-described methods, the first or second CAS9 mutant can be a D10A or H840A mutant version of SEQ ID NO.: 1 as disclosed below. The strand-displacing nucleic acid polymerase can be a φ29 DNA polymerase. The detecting agent can be a nucleotide probe, e.g., a molecular beacon probe or a Yin-Yang probe that is labeled with a fluorophore and a quencher. When fluorophores are used, the detecting step can be carried out by measuring the fluorescent signal emitted upon hybridization of the probe to a region or sequence complementary to the tag region.

In some embodiment, the one or more copies, which contain the second CAS-targeted site, can also contain the first PAM site. The one or more extension products created using the circular probes as templates can contain the second CAS-targeted site. In some embodiments, the target nucleic acid strand is on one strand of a genomic DNA of a pathogenic or non-pathogenic microorganism (such as a virus, a bacterium, and a fungus) or a genomic DNA in a cell of a subject such as a plant or an animal (e.g., a human). In that case, the sample contains the microorganism or cell and the method further comprises lysing the microorganism or the cell before step (a) or (b). The target nucleic acid strand can contain a mutation of the subject, e.g., a translocation or an inversion.

In a second aspect, the invention provides an in vitro, cell-free composition containing a first CAS9 mutant having a single-strand nicking activity and a first gRNA. The composition can further contain one or more reagents selected from the group consisting of a strand-displacing nucleic acid polymerase, nucleotides, a second CAS9 mutant having a single-strand nicking activity, a second gRNA, a detecting agent, and a circular probe. The first gRNA and the second gRNA target a first CAS-targeted site and a second CAS-targeted site of a target nucleic acid strand of interest, respectively, where the first target sequence is different from the second target sequence. The circular probe has (i) a CAS region that is substantially complementary to the second CAS-targeted site and (ii) a tag region. A complementary sequence of the tag region is recognizable by the detecting agent.

In the above-described methods and compositions, the first CAS9 mutant and the first gRNA can be provided separately or provided in the form of a protein-RNA complex. Similarly, the second CAS9 mutant and the second gRNA can be provided separately or in a pre-formed protein-RNA complex. The two CAS9 mutants can be of the same type of mutant or two different types of mutants. In the latter case, the two mutants preferably nick the same nucleic acid strand. The detecting agent can be a nucleotide probe, such as a molecular beacon probe or a Yin-Yang probe that is labeled with a fluorophore and a quencher. Also provided is a kit containing one, two, or more of the above described reagents.

The details of one or more embodiments of the invention are set forth in the description below. Other features, objects, and advantages of the invention will be apparent from the description and from the claims.

DETAILED DESCRIPTION OF THE INVENTION

Figure 1:
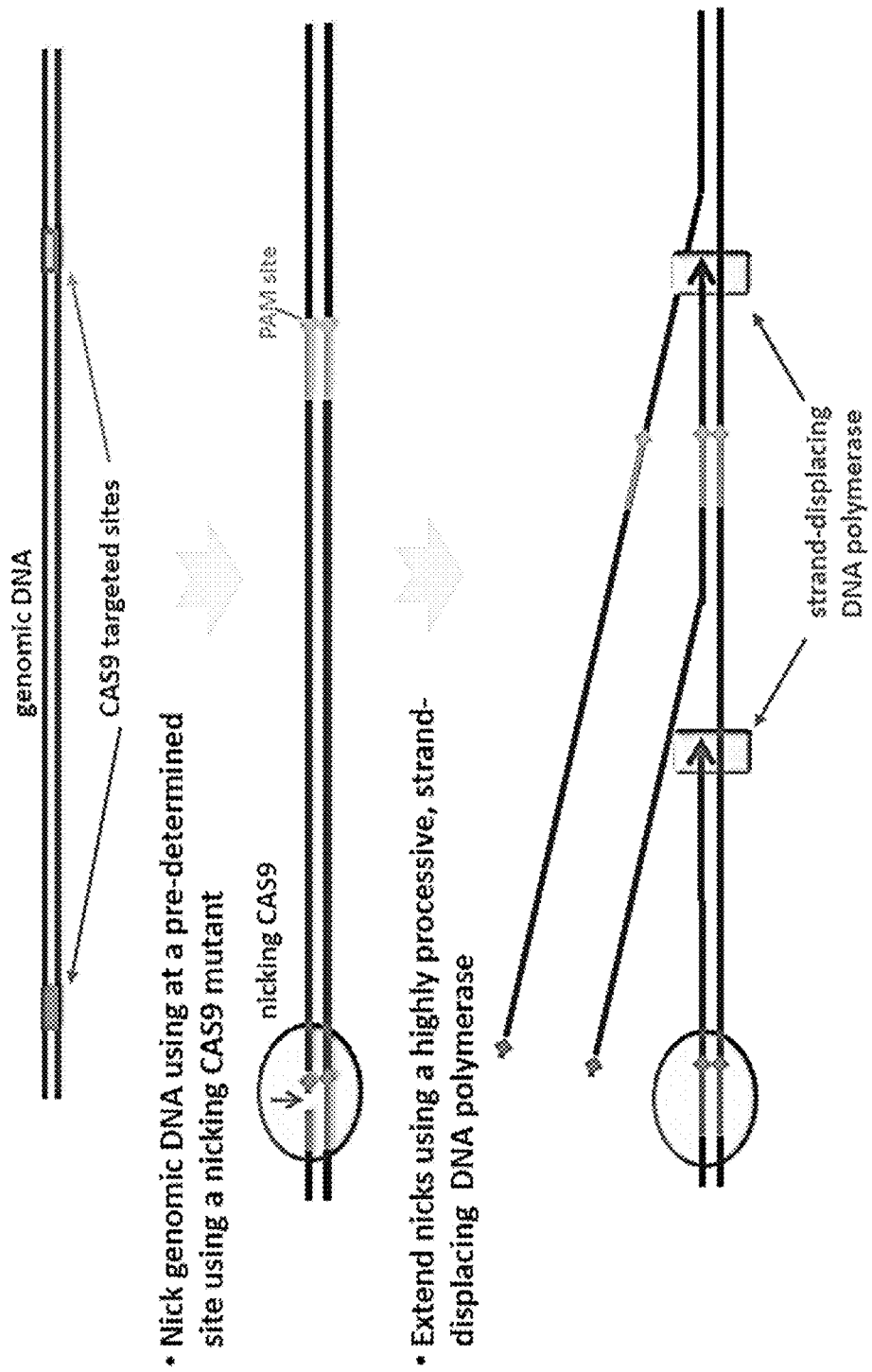
FIG. 1 is a diagram showing induction of strand displacement of a genomic analyte by nicking with a CAS9 mutant in conjunction with DNA polymerization by a strand displacing DNA polymerase.

This invention is based, at least in part, on an unexpected discovery that the CRISPR/CAS nucleic acid targeting system in connection with a strand displacing DNA polymerase can be used in isothermal amplification and allows one to overcome the low specificity limitation in conventional isothermal amplification techniques.

Various conventional isothermal nucleic acid amplification techniques are known in the art. Examples include nicking and extension amplification reaction (NEAR), recombinase polymerase amplification (RPA), isothermal and chimeric primer-initiated amplification of nucleic acids (ICAN), transcription-mediated amplification (TMA), nucleic acid sequence-based amplification (NASBA), signal-mediated amplification of RNA technology (SMART), strand-displacement amplification (SDA), rolling circle amplification (RCAT), ligase amplification reaction, loop-mediated isothermal amplification of DNA (LAMP), isothermal multiple displacement amplification, helicase-dependent amplification (HDA), single primer isothermal amplification (SPIA), and circular helicase-dependent amplification. These isothermal amplification methods are discussed in, e.g., Gill et al., Nucleosides Nucleotides Nucleic Acids 2008 27:224-243; Mukai et al., 2007, J. Biochem. 142:273-281; Van Ness et al., PNAS 2003 100: 4504-4509; Tan et al., Anal. Chem. 2005, 77:7984-7992; Lizard et al., Nature Biotech. 1998, 6:1197-1202; Mori et al., J. Infect. Chemother. 2009 15:62-69; Notomi et al., NAR 2000, 28:e63; and Kurn et al., Clin. Chem. 2005, 51:10, 1973-1981. Other references for these general amplification techniques include, for example, U.S. Pat. Nos. 7,112,423; 5,455,166; 5,712,124; 5,744,311; 5,916,779; 5,556,751; 5,733,733; 5,834,202; 5,354,668; 5,591,609; 5,614,389; and 5,942,391; and 520030082590, US20030138800, US20040058378, US20060154286, US20090081670, US 20090017453 and US20130330777. All of the above documents are incorporated herein by reference.

The above conventional amplification reactions typically use one or more enzymes and involve annealing primers to their targets at temperature much lower than those for PCR. As a result, the primer-target annealing or hybridization is less stringent and has specificity lower than that in PCR. As disclosed here, this limitation can be overcome by utilizing the CRISPR/CAS9 system and two independent CAS9-based initiation events.

CRISPR System

CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage. Three types of CRISPR systems have been identified across a wide range of bacterial hosts. A functional bacterial CAS9/CRISPR system requires three components: the CAS9 protein which provides the nuclease activity and two short, non-coding RNA species referred to as CRISPR RNA (crRNAs) and trans-acting RNA (tracrRNA).

One key feature of each CRISPR locus is the presence of an array of repetitive sequences (direct repeats) interspaced by short stretches of non-repetitive sequences (spacers). To license the associated CAS nuclease for nucleic acid cleavage, the non-coding CRISPR array is transcribed and cleaved within direct repeats into short CRISPR RNA (crRNAs) containing individual spacer sequences, which direct CAS nucleases to the target site (protospacer).

The Type II CRISPR is one of the most well characterized systems and carries out targeted DNA double-strand break in four sequential steps. First, two non-coding RNA, the pre-crRNA and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs CAS nuclease the target DNA via Wastson-Crick base-pairing between the spacer on the crRNA and the protospacer on the target DNA next to a so-called protospacer adjacent motif (PAM), an additional requirement for target recognition. Finally, CAS nuclease mediates cleavage of target DNA to create a double-stranded break within the target site, i.e., protospacer.

The PAM is present on the target strand, but not the crRNA that's produced to target it. This arrangement prevents self-cleavage of the CRISPR arrays. Type II CRISPR system, one of the most well characterized systems, uses target sequences that are N12-20NGG, where NGG represent the PAM site from *S. thermophiles* and *S. pyogenes*. Additional PAM site sequences include those from *N. meningitidis* NNNNGATT, *S. thermophilus* NNAGAA and *T. denticola* NAAAAC. See, e.g., WO 2013176772, Cong et al., (2012), Science 339 (6121): 819-823, Jinek et al., (2012), Science 337 (6096): 816-821, Mali et al, (2013), Science 339 (6121): 823-826, Gasiunas et al., (2012), Proc Natl Acad Sci USA. 109 (39): E2579-E2586, Cho et al., (2013) Nature Biotechnology 31, 230-232, Hou et al., Proc Natl Acad Sci USA. 2013 Sep. 24; 110(39):15644-9, Mojica et al., Microbiology. 2009 March; 155(Pt 3):733-40, and http://www.addgene.org/CRISPR/.

The bacterial CAS9/CRISPR (also referred to as CRISPR/CAS9) system targets specific DNA sequences, typically corresponding to invading bacteriophages or plasmids, for destruction by inducing double strand breaks corresponding to a crRNA encoded by the CAS9/CRISPR system. As mentioned above, the system includes two RNAs and one nuclease.

1. RNAs

A crRNA is processed from pre-crRNA array, an array of variable sequences of constant size (spacers) separated by a repeat sequence that serves as processing signal. The tracrRNA binds to the CRISPR/repeats and triggers RNAseIII-mediated processing of the pre-crRNA into monomers, i.e., spacer RNAs consisting of the spacer sequence that corresponds to the targeted DNA and a dsRNA part corresponding to part of the CRISPR repeat and the annealed tracrRNA. The tracrRNA and spacer RNA together can be referred as guide RNA (gRNA). The two RNA species can be joined to form on hybrid RNA molecule referred to as small guide RNA (sgRNA). When complexed with CAS9, the CAS9-guide RNA complex could find and cut the correct DNA targets. Pennisi, E. (2013) Science 341 (6148): 833-836.

2. CAS9 Protein

CAS9 protein is a nuclease, an enzyme specialized for cutting DNA. Once associated with the tracrRNA and crRNA (i.e., guide RNA), it is guided by the spacer in the crRNA to target specific DNA sequence (i.e., protospacer sequence). The CAS9 protein has two separate domains for DNA cleavage, one for the strand paired with the guide RNA and another separate domain for cleavage of the unpaired strain. One or both of the domains/sites can be modified or mutated while preserving the CAS9's ability to home located its target DNA. Accordingly, mutations inactivating (or a least greatly diminishing) the activity of either domain result in a DNA nicking enzyme or, if both domains are mutated, in a DNA binding protein.

CAS9 activity can be reconstituted in vitro with only the CAS9 protein, the guide RNA and a suitable buffer required for activity. Co-expression of the CAS9 protein with the guide RNA is sufficient to induce DNA cleavage of a DNA sequence corresponding to the spacer part of the guide RNA provided that a permission signal, i.e., the PAM sequence is present 3' to the target sequence. The exact nature of the PAM site varies between CAS9 systems. For the best characterized CAS9 system from *Streptococcus pyogenes* it is NGG.

In a mature CAS9-guide RNA complex, the target-matching spacer sequence is about 20 nt long, suggesting a specificity of $4^{22}$ (including the 2 nucleotides from the PAM sequence) or 1 occurrence in $1.7 \times 10^{10}$ base pairs. However, the CAS9 system tolerates mismatches of the guide RNA with the target and in vivo data suggest that a match of 15 nucleotides may be sufficient for cleavage. This would still result in a specificity of $1-10 \times 10^7$ base pairs. As disclosed herein, utilizing two independent CAS9-based initiation events in isothermal amplification, one can achieve even higher specificity. In addition, due to the PAM site requirement, each of the events is expected to have at least 2-nt larger specificity than provided by the RNA/DNA-based annealing.

Detection Methods

This invention provides methods for detection of specific DNA sequences in a complex sample, e.g., genomic sample, by isothermal amplification utilizing the specificity provided by the CRISPR/CAS9 system by coupling two independent CAS9 nicking events for signal generation.

Figure 2:
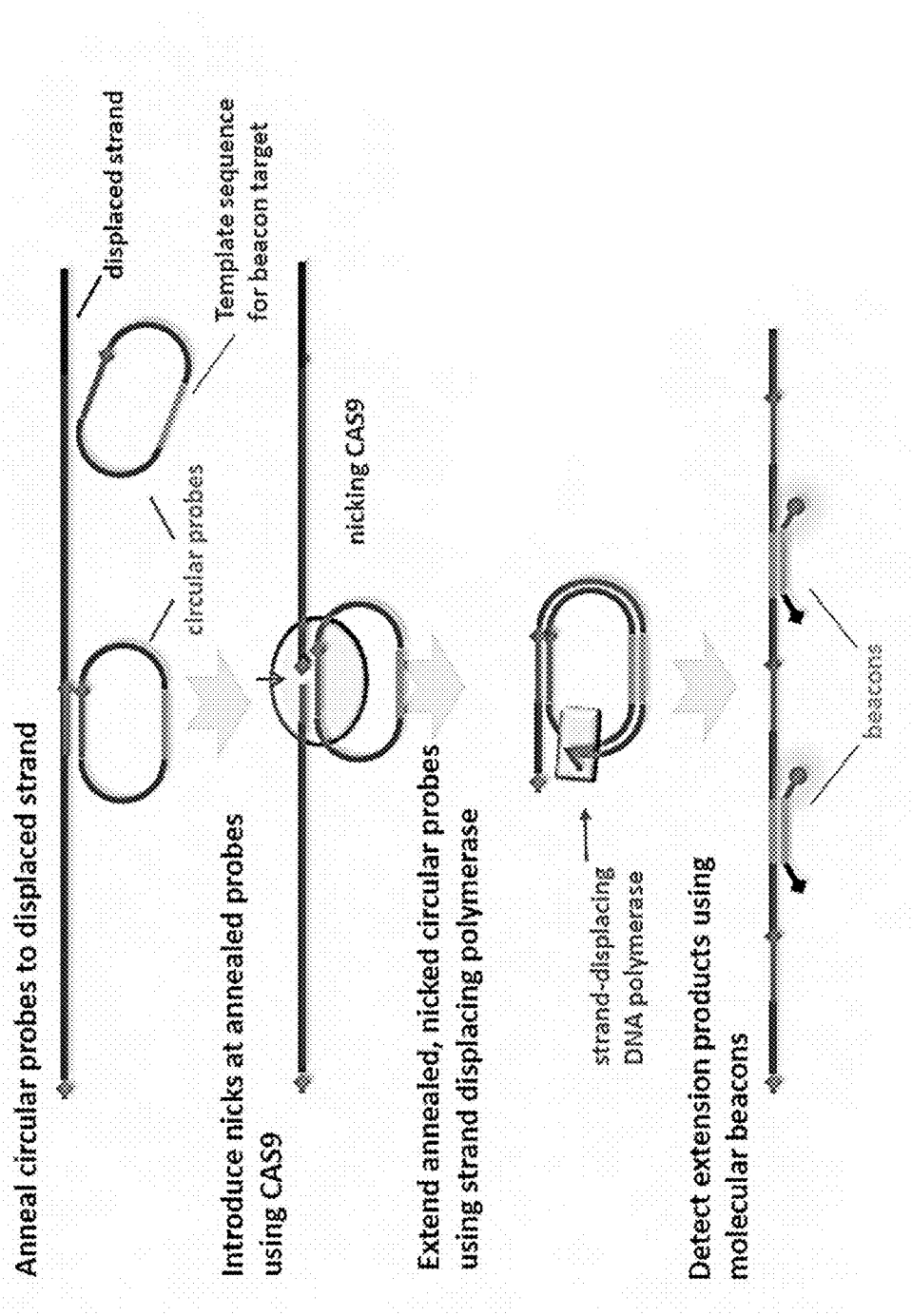
FIG. 2 is a diagram showing detection of a specific DNA sequence within the displaced genomic DNA strand using circular templates, a nicking mutant of CAS9, a strand-displacing DNA polymerase, and detection probes.

Referring to FIGS. 1 and 2, in one embodiment of the invention, the method for detection comprises two steps. In the first step, a target or analyte (e.g., a genomic target) is nicked at a known site using a nicking mutant of CAS9 such as the D10A or H840A mutants of *S. pyogenes* CAS9. Extension of the nick with a highly processive, strand-displacing DNA polymerase such as φ29 DNA polymerase leads to displacement of the DNA strand 3' to the nicking site. Since the nicking site is restored by the extension, repeated nicking and extension cycles result in linear amplification displaced strands.

In the second step, the displaced strand is hybridized to a circular probe, reconstituting a second CAS9-targetable site (e.g., providing a suitable PAM site) (see FIG. 2). Nicking of the displaced strand annealed to the circular probe and extension of the nick by a strand displacing DNA polymerase leads to formation of concatenated repeated sequences that can be detected using probes such as molecular beacons. It should be pointed that the annealing to circular probes displaced concatenated sequences reconstitutes the second CAS9 nicking site, resulting in an exponential increase of the number of active strand-displacing replication forks.

The generation of signal using the above method is dependent on two independent CAS9 cleavage events thus increasing the specificity of detection. The signal generated by this method, e.g., fluorescence increase, can be easily detected by a variety of devices such as QPCR instruments. For quantitative applications it may be advantageous to utilize a highly compartmentalized parallel detection system (e.g. akin to "digital PCR"). In the methods, the two steps can be carried out either separately in separate reaction mixtures or concurrently in a same reaction mixture. In preferred embodiments, the two steps are carried out concurrently in a same reaction mixture.

1. Target Nucleic Acid Strand and Related gRNAs

The method of this invention allows one to detect any target nucleic acid strand of interest as long as the sequences of two segments (referred herein as a first target sequence and a second target sequence) of such a strand are known and can be used to design two different, specific crRNAs/guide RNAs. FIG. 1 depicts a schematic representation of an embodiment of a target nucleic acid strand that can be detected using the CAS9 mutant-assisted target DNA strand amplification disclosed herein. In the embodiment, the target nucleic acid strand corresponds to the upper one of the two strands, and this target nucleic acid strand has two CAS-targeted sites, a first/5' CAS-targeted site on the left and a second CAS-targeted site on the right.

Another requirement for the target nucleic acid strand is that the strand has two PAM sites/sequences 3' to the two segments respectively so that two different, specific crRNAs/guide RNAs can be designed based on the two target sequences to complex with suitable CAS9 proteins, which can nick (i.e., generate a break) in that strand. Each target sequence and its corresponding 3' PAM site/sequence is referred herein as a CAS-targeted site (e.g., a first CAS-targeted site and a second CAS-targeted site).

The target nucleic acid strand can be one of the two stands on a genomic DNA in a host cell. Examples of such genomic dsDNA include, but are not necessarily limited to, a host cell chromosome and a stably maintained plasmid. However, it is to be understood that the present method can be practiced on other dsDNA present in a host cell, such as non-stable plasmid DNA, viral DNA, and phagemid DNA, as long as there are two different CAS-targeted sites regardless of the nature of the host cell dsDNA.

As shown in FIGS. 1 and 2, the method of the invention involves at least two independent CAS9 nicking events. Therefore, at least two different pre-defined CAS-targeted sites/sequences in the target nucleic acid strand must be identified so that the two guide RNAs do not target the same sequence. As mentioned above, the targeting specificities of the two sites are provided by the combination of the guide RNA sequences and the PAM site sequences.

Type II CRISPR system, one of the most well characterized system, uses target sequences that are N12-20NGG, where NGG represent the PAM site. In an organism with a 50% GC content, such targetable sites are expected every 32 base pairs. Accordingly, the method of this invention can be used on any target nucleic acid of interest that is 64 base pairs or longer. Other suitable PAM sites can also be used in conjunction with corresponding CRISPR/CAS system to practice this invention. In preferred embodiments of this invention, the pre-determined sites contain one or more pre-defined cleavage sequences for a dsDNA CRISPR/CAS system, such as the CRISPR/CAS9 system of *S. pyogenes* and *S. thermophilus*.

Once a nick is generated, the nicked targeted nucleic acid strand functions as a primer for primer extension. Extension of the nick with a highly processive, strand-displacing DNA polymerase (e.g., φ29 DNA polymerase) leads to displacement of the DNA strand 3' to the nicking site. Since the nicking site is restored by the extension, repeated nicking and extension cycles result in linear amplification displaced strands.

It is known in the art that cleavage sequences for natural CRISPR/CAS systems exist, and that these sequences vary from organism to organism and from strain to strain. The key sequences for successful detecting the nucleic acid strand is the targeted sequence (much of the sequence of which may vary), and in particular the 12 or so nucleotides on the 3' end of the targeted sequence, and the PAM sequence. The targeted sequence allows for identification of the sequence to nick, while the PAM and 3' end region of the targeted sequence allow for specificity and activity. In view of the general knowledge regarding various known CRISPR/CAS systems, it is a simple matter to select a system, identify a CAS-targeted site for that system, and design a corresponding crRNA or guide RNA.

Having a knowledge of the sequence of the target nucleic acid allows the practitioner to generate suitable spacer RNA and related CAS9-guide RNA complex. One or more different complexes targeting different sites can be generated. There are no particular considerations to address between the various dsDNA CRISPR/CAS systems, and the practitioner is free to select a desired system as a matter of design choice. The only limitation is that there must be at least two different pre-defined CAS-targeted sites.

This can be accomplished in any number of ways, as will be immediately apparent to the skilled artisan. For example, it is envisioned that the most straightforward way is to consult one or more nucleic acid databases to determine the natural sequence of a site of interest and then determine if two CAS-targeted sites exist within that site of interest. In other words, in embodiments of the invention, identifying CAS-targeted sites at a pre-determined site on a target nucleic acid can be accomplished by identifying the nucleotides (e.g., 30 nt in length) 5' of a PAM sequence that is present on the target nucleic acid, then engineering a CRISPR array to include those nucleotides as a spacer sequence. According to the current state of the art, substantially all genomic sites of interest have been defined and their sequences determined.

As CAS9-guide RNA complexes target double stranded DNA, the method of this invention is particularly useful for detecting a double stranded DNA. Accordingly, potential applications for the disclosed method include fast detection of translocations or inversions in a genome. Yet, one skilled in the art would appreciate that the method of this invention can be used for detecting a target nucleic acid template, which is single-stranded, such as single-stranded RNA (ssRNA) or single-stranded DNA (ssDNA). For example, in isothermal amplification embodiments that use RNA templates, the system may also include an enzyme having reverse transcriptase (RT) activity, a primer capable of being hybridized to the ssRNA, and a means for cleaving the single-stranded RNA template. As such, a double-stranded nucleic acid template containing a target of interest can be obtained as a product of the RT reaction from the ssRNA template for subsequent analysis by the isothermal amplification.

2. CAS9-Guide RNA Complex

The invention requires two CAS9-guide RNA complexes. Each complex in general includes three components: (i) a component for enzymatic nicking of a target double-stranded nucleic acid at a specific sequence, (ii) a targeting component comprising a spacer sequence, which directs a nicking complex to the correct sequence, and (iii) a tracr component. The targeting component and the tracr component can be two separate RNA molecules or joined as one hybrid RNA molecule.

The CAS9-guide RNA complexes can be made using recombinant technology using a host cell system or an in vitro translation-transcription system known in the arty. Detailed of such system and technology can be found in e.g., WO2013176772 and U.S. 61/775,510, the contents of which are incorporated herein by reference in their entireties. CAS9-guide RNA complexes can be isolated or purified, at least to some extent, from cellular material of a cell or an in vitro translation-transcription system in which they are produced.

In some exemplary embodiments, a CAS9-guide RNA complex is provided as a ready-to-use combination comprising a component for enzymatic nick of a target double-stranded nucleic acid at a cleavage sequence, such as a mutant form of the CAS9 protein of *S. pyogenes* or *S. thermophilus*, and a RNA processed form of a CRISPR array, which includes a processed spacer or guide RNA. In certain embodiments, a tracrRNA is also provided, either as a separate component or as an element fused to the spacer RNA. The tracrRNA can be defined as a short, non-coding RNA that is required for processing of the crRNA into guide RNA and for CAS-mediated cleavage of the target DNA. The tracrRNA has a section that anneals to the CRISPR repeat to initiate processing by the host enzyme RNAse III. As currently understood, the primary sequence of the CRSIPR repeats of the CAS9 system are of minor importance. What matters more is the structure formed by annealing of the tracrRNA to the CRISPR repeat (e.g., the differences between the CRSIPR sequences of different CAS9 systems are matched by a corresponding difference in their tracrRNA).

3. CAS9 Mutant/Variant

The above-mentioned protein component for enzymatic nicking of a target double-stranded nucleic acid can be a variant or mutant form of a CRSIPR protein having Cas9 activity, e.g., CAS9. That is, the enzymatic component has a DNA nicking activity. As used herein, an enzyme having DNA nicking activity refers to an enzyme, e.g., a CAS9 variant or mutant, that can cleave the two strands of a DNA at different levels. Shown below are the amino acid sequences of a wild type *Streptococcus pyogenes* CAS9 protein and two variants with nicking activity, where the sites for two amino acid substitutions are underlined.

```
S. pyogenes CAS9 (wild type; SEQ ID NO: 1):
MDKKYSIGLDIGTNSVGWAVITDDYKVPSKKFKVLGNTDRHSIKKNLIGALLFGSGETAEATRLKRTA

RRRYTRRKNRICYLQEIFSNEMAKVDDSFFHRLEESFLVEEDKKHERHPIFGNIVDEVAYHEKYPTIY

HLRKKLADSTDKADLRLIYLALAHMIKFRGHFLIEGDLNPDNSDVDKLFIQLVQIYNQLFEENPINAS

RVDAKAILSARLSKSRRLENLIAQLPGEKRNGLFGNLIALSLGLTPNFKSNFDLAEDAKLQLSKDTYD

DDLDNLLAQIGDQYADLFLAAKNLSDAILLSDILRVNSEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGAYHDLLKIIKDKDFLDNEEN

EDILEDIVLTLTLFEDRGMIEERLKTYAHLFDDKVMKQLKRRRYTGWGRLSRKLINGIRDKQSGKTIL
```

-continued

DFLKSDGFANRNFMQLIHDDSLTFKEDIQKAQVSGQGHSLHEQIANLAGSPAIKKGILQTVKIVDELV

KVMGHKPENIVIEMARENQTTQKGQKNSRERMKRIEEGIKELGSQILKEHPVENTQLQNEKLYLYYLQ

NGRDMYVDQELDINRLSDYDVDHIVPQSFIKDDSIDNKVLTRSDKNRGKSDNVPSEEVVKKMKNYWRQ

LLNAKLITQRKFDNLTKAERGGLSELDKAGFIKRQLVETRQITKHVAQILDSRMNTKYDENDKLIREV

KVITLKSKLVSDFRKDFQFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVVAKVEKGKSKKL

KSVKELLGITIMERSSFEKNPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQISEFSKRVILADANLDKVLSA

YNKHRDKPIREQAENIIHLFTLTNLGAPAAFKYFDTTIDRKRYTSTKEVLDATLIHQSITGLYETRID

LSQLGGD

*S. pyogenes* CAS9 D10A mutant (nicking enzyme, SEQ ID NO: 2):
MDKKYSIGLAIGTNSVGWAVITDDYKVPSKKFKVLGNTDRHSIKKNLIGALLFGSGETAEATRLKRTA

RRRYTRRKNRICYLQEIFSNEMAKVDDSFFHRLEESFLVEEDKKHERHPIFGNIVDEVAYHEKYPTIY

HLRKKLADSTDKADLRLIYLALAHMIKFRGHFLIEGDLNPDNSDVDKLFIQLVQIYNQLFEENPINAS

RVDAKAILSARLSKSRRLENLIAQLPGEKRNGLFGNLIALSLGLTPNFKSNFDLAEDAKLQLSKDTYD

DDLDNLLAQIGDQYADLFLAAKNLSDAILLSDILRVNSEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGAYHDLLKIIKDKDFLDNEEN

EDILEDIVLTLTLFEDRGMIEERLKTYAHLFDDKVMKQLRRRYTGWGRLSRKLINGIRDKQSGKTIL

DFLKSDGFANRNFMQLIHDDSLTFKEDIQKAQVSGQGHSLHEQIANLAGSPAIKKGILQTVKIVDELV

KVMGHKPENIVIEMARENQTTQKGQKNSRERMKRIEEGIKELGSQILKEHPVENTQLQNEKLYLYYLQ

NGRDMYVDQELDINRLSDYDVDHIVPQSFIKDDSIDNKVLTRSDKNRGKSDNVPSEEVVKKMKNYWRQ

LLNAKLITQRKFDNLTKAERGGLSELDKAGFIKRQLVETRQITKHVAQILDSRMNTKYDENDKLIREV

KVITLKSKLVSDFRKDFQFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVVAKVEKGKSKKL

KSVKELLGITIMERSSFEKNPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQISEFSKRVILADANLDKVLSA

YNKHRDKPIREQAENIIHLFTLTNLGAPAAFKYFDTTIDRKRYTSTKEVLDATLIHQSITGLYETRID

LSQLGGD

*S. pyogenes* CAS9 H839A mutant (nicking enzyme, SEQ ID NO: 3):
MDKKYSIGLDIGTNSVGWAVITDDYKVPSKKFKVLGNTDRHSIKKNLIGALLFGSGETAEATRLKRTA

RRRYTRRKNRICYLQEIFSNEMAKVDDSFFHRLEESFLVEEDKKHERHPIFGNIVDEVAYHEKYPTIY

HLRKKLADSTDKADLRLIYLALAHMIKFRGHFLIEGDLNPDNSDVDKLFIQLVQIYNQLFEENPINAS

RVDAKAILSARLSKSRRLENLIAQLPGEKRNGLFGNLIALSLGLTPNFKSNFDLAEDAKLQLSKDTYD

DDLDNLLAQIGDQYADLFLAAKNLSDAILLSDILRVNSEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

-continued

```
KKAIVDLLFKTNRKVTVKQLKEDYFKKIECFDSVEISGVEDRFNASLGAYHDLLKIIKDKDFLDNEEN

EDILEDIVLTLTLFEDRGMIEERLKTYAHLFDDKVMKQLKRRRYTGWGRLSRKLINGIRDKQSGKTIL

DFLKSDGFANRNFMQLIHDDSLTFKEDIQKAQVSGQGHSLHEQIANLAGSPAIKKGILQTVKIVDELV

KVMGHKPENIVIEMARENQTTQKGQKNSRERMKRIEEGIKELGSQILKEHPVENTQLQNEKLYLYYLQ

NGRDMYVDQELDINRLSDYDVDAIVPQSFIKDDSIDNKVLTRSDKNRGKSDNVPSEEVVKKMKNYWRQ

LLNAKLITQRKFDNLTKAERGGLSELDKAGFIKRQLVETRQITKHVAQILDSRMNTKYDENDKLIREV

KVITLKSKLVSDFRKDFQFYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVVAKVEKGKSKKL

KSVKELLGITIMERSSFEKNPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQISEFSKRVILADANLDKVLSA

YNKHRDKPIREQAENIIHLFTLTNLGAPAAFKYFDTTIDRKRYTSTKEVLDATLIHQSITGLYETRID

LSQLGGD
```

The H839A mutant is same as the H840A mutant described in Jinek et al. 2010 *Science* 337 (6096): 816-821. Due to a counting error in Jinek et al., this mutation was referred to as H840A in the literature. Using correct numbering the mutation should be referred to as H839A.

In some cases, the enzyme variant can cleave the strand complementary to the spacer RNA (i.e., the bottom strand shown in FIGS. 1 and 2) effectively, but has reduced ability to cleave the non-complementary strand of the target DNA. For example, the variant can have a mutation (e.g., amino acid substitution) that reduces the function of the RuvC domain and as a result reduces the ability to cleave the non-complementary strand of the target DNA. As a non-limiting example, in some cases, the variant CAS9 site-directed polypeptide is a D10A (aspartate to alanine) mutation of the amino acid sequence depicted in SEQ ID NO: 2 (or the same substitution at the site equivalent to D10 of CAS enzymes for other species).

In some other cases, the variant can cleave the non-complementary strand of the target DNA (i.e., the top strand shown in FIGS. 1 and 2) effectively but has reduced ability to cleave the complementary strand. For example, the variant can have a mutation (e.g., amino acid substitution) that reduces the function of the HNH domain. As a non-limiting example, in some cases, the variant CAS9 site-directed polypeptide is a H839A (histidine to alanine at amino acid position 839 of SEQ ID NO: 1, as shown in SEQ ID NO: 3) or the same substitution at the site equivalent to H839 of CAS enzymes for other species. See Jinek et al. 2010 *Science* 337 (6096): 816-821, which is incorporated herein by reference.

One skilled in the art would understand that when CAS9 variants having activity similar to that of H839A are used, the target dsDNA is nicked at the strand that is not complementary to the spacer RNA, i.e., the top strand shown in FIG. 1. In that case, the left and right CAS-targeted sites shown in FIG. 1 correspond to the above-mentioned first CAS-targeted site and second CAS-targeted site. Accordingly, the related nicking, strand displacing, and hybridization events take place in the manner shown in FIGS. 1 and 2.

Vice versa, when variants having activity similar to that of the D10A mutant are used, the target dsDNA is nicked in the strand that is complementary to the spacer RNA, i.e., the bottom strand shown in FIG. 1. In this case, the bottom strand corresponds to the above-mentioned target nucleic acid strand. Accordingly, the right CAS-targeted site in FIG. 1 corresponds to the above-mentioned first CAS-targeted site/5' CAS targeted site, while the left CAS-targeted site in FIG. 1 corresponds to the above-mentioned second CAS-targeted site/3' CAS targeted site. Under this scenario, the related nicking, strand displacing, and hybridization events take place on the strand complementary to that shown in FIGS. 1 and 2, and the related extensions proceed in the directions opposite to those shown in FIGS. 1 and 2.

In any event, the skilled in the art would understand that method of this invention can be practiced in either situation. He or she would be able to design and use two independent CAS9-based initiation events and related reagents (such as the circular probes) accordingly.

4. Isothermal Amplification/Strand-Displacing Nucleic Acid Polymerase

Once a strand is nicked, the 3' end serves as the starting point for DNA polymerase to begin synthesis of a new DNA strand. As used herein a "polymerase" means an enzyme capable of catalyzing template dependent oligonucleotide extension by conjugating extension nucleotides to an oligonucleotide or amplicon. In isothermal amplification processes, the polymerase generally promotes strand displacement, which refers to the ability of a polymerase to displace downstream DNA encountered during primer extension. DNA polymerases having strand displacement activity include those of φ29 DNA polymerase, DNA polymerase I, Klenow fragment, Klenow fragment (3'->5' exo-), DNA polymerases isolated or derived from thermophilic organisms, e.g., VENT® DNA Polymerase, 9°Nm DNA Polymerase, Therminator DNA Polymerase, and *Bacillus stearothermophilus* (Bst) DNA polymerase (see U.S. Pat. Nos. 5,874,282; 6,100,078, and 6,066,483). In preferred embodiments, a DNA polymerase may be modified to reduce, inhibit, inactivate or remove its 5' exonuclease activity (i.e., 5'-exo-minus polymerase). Preferred polymerases include those that tolerate modified oligonucleotides and/or modified extension nucleotides when catalyzing oligonucleotide extension. Typically, during nucleic acid amplification, a nucleic acid polymerase adds nucleotides to the 3' end of a primer using the complementary nucleic acid strand as a template, thereby synthesizing a strand that includes a sequence partially or completely identical to the target nucleic acid strand.

The bottom panel in FIG. 1 depicts a schematic representation of an embodiment of CAS9 mutant-assisted target DNA strand amplification. Upon nicking of the upper target DNA strand by a CAS9 mutant (shown as "nicking CAS9"), the nicked strand with the free 3' end serves as a primer and the DNA polymerase (e.g., a 5'→3 exonuclease-deficient Bst DNA polymerase) extends the primer by generating a double stranded DNA (primer extension product). The extension reaction further creates and duplicates a copy of the first CAS-targeted site having the first target sequence and the first PAM site 3' to the first target sequence. This creates a second a site for the CAS9 mutant/gRNA complex, which is capable of targeting this site and creating another single stranded nick a position 3' to the PAM site. The CAS9 mutant nicks the double stranded DNA at this nicking site. Nicking creates a new DNA synthesis initiation site for the DNA polymerase. The DNA polymerase binds to this initiation site and further elongates the nicked target strand, which serves as another primer. Since the DNA polymerase has strand displacement activity, it displaces a single-stranded DNA product while it re-creates the double-stranded primer extension product. This cycle repeats, synthesizing multiple single strands of DNA complementary to the downstream portion of the target DNA strand.

The schematic representation of a nucleic acid amplification shown in FIG. 1 may be varied by employing additional enzymes, additional nucleotides, stains, dyes, or other labeled components. For example, amplification may be carried out using labeled nucleotides to monitor the CAS9 mutant-assisted target DNA strand amplification.

The nucleic acid amplification shown in FIG. 1 synthesizes multiple single stranded copies of the target nucleic acid strand corresponding to the downstream portion of the first CAS targeted sites. These multiple single strands should contain the sequence for the second CAS-targeted site. And these second CAS-targeted site-containing strands serve as the strands to be nicked for a second round of CAS9 mutant-assisted target DNA strand amplification.

The top three panels in FIG. 2 depict a schematic representation of an embodiment of this second round of CAS9 mutant-assisted target DNA strand amplification. Unlike the first round, one or more circular probes are used as the template. To that end, each of the circular probes contains the sequence complementary to that of the second CAS-targeted site, which contains a second target sequence and a second PAM site 3' to the second target sequence. To achieve two independent CAS9-based initiation events, the second target sequence should be different from the first target sequence.

As will be appreciated, the term "circular" when referring to the strand configuration merely denotes a strand of a nucleic acid that includes no terminal nucleotides, and does not necessarily denote any geometric configuration.

To create dsDNAs for this second CAS9-based initiation event, the one or more circular probes are contacted with the multiple single strands of the target nucleic acid strand synthesized in the first round of CAS9 mutant-assisted target DNA strand amplification under conditions permitting annealing or hybridization between the circular probes and the synthesized single strands. This hybridization process results in nucleic acids having portions of duplexes, recreating the site that is same as the second CAS9-targeted site, which can be targeted by a second CAS9 mutant/gRNA complex.

As shown in FIG. 2, once the circular probes are annealed and the second CAS9-targeted site forms, CAS9 mutant/gRNA complex specific for the second CAS9-targeted site nicks the upper, target DNA strand in a manner similar to that shown in FIG. 1. Again, the nicked strand with the free 3' end serves as a primer and the DNA polymerase extends the primer by generating a double stranded DNA primer extension product. Like that in the first round, the extension reaction creates copies of the second CAS-targeted site (including the second target sequence and the second PAM site). Unlike that in the first round, the strand-displacing DNA polymerase rolls along the circular probe template and generate primer extension product that has a sequence complementary to that of the probe template. This cycle repeats, synthesizing one long single stranded DNA having multiple copies of sequence complementary to that of the probe template. These complementary sequences can be detected using any suitable detection methods and detection probes.

5. Detection

Any suitable detection probe may be used to detect amplification products by hybridizing to the amplification product and producing a detectable signal. A detection probe may be used simultaneously with the above-described amplifications in a reaction or may contact the amplification product subsequent to amplification. A probe may be a nucleic acid that hybridizes to a sequence to be detected (target sequence) including hybridization between DNA/DNA, or between strands in which one or both strands contain at least one modified nucleotide, nucleoside, nucleobase, and/or base-to-base linkage. Two single strands of sufficient complementarity may hybridize to form a double-stranded structure in which the strands are joined by hydrogen bonds between complementary base pairs (e.g., A with T or U, and G with C) at any point along the hybridized strands. That is, under conditions that promote hybridization between complementary bases, sufficient bonding results in a double-stranded nucleic acid. The rate and extent of hybridization are influenced factors that are well known in the art, which may be predicted by mathematical calculations related to the melting temperature (Tm) for a given hybrid and hybridization solution used, or may be determined empirically by using standard methods known in the art. Some embodiments of probe sequences are selected to contain no or a minimum of self-complementarity, whereas other probe embodiments may be partially self-complementary to facilitate detection of probe:target duplexes in a sample without removing unhybridized probe before detection.

Examples of partially complementary probes are known, e.g., "molecular beacon" or "molecular switch: probes (e.g., U.S. Pat. Nos. 5,118,801, 5,312,728, 5,925,517 and 6,150,097, and Giesendorf et al., 1998, Clin. Chem. 44 (3):482-6) and "molecular torch" probes (e.g., U.S. Pat. No. 6,361,945). All of these references are incorporated by reference in their entireties. Such probes typically include interacting labels (e.g., luminescent/quencher or fluorophore/quencher pairs) positioned so that a different signal is produced when the probe is self-hybridized compared to when the probe is hybridized to a target nucleic acid.

Detection probes typically have one or more regions of sufficient complementary to hybridize with the target nucleic acid sequence, or its complement, under stringent hybridization conditions (e.g., 60° C. in a solution with a salt concentration of about 0.6-0.9 M). A variety of hybridization conditions are well known in the art (e.g., Molecular Cloning: A Laboratory Manual, Fourth Edition, 2012, Cold Spring Harbor Laboratory Press, Cold Spring Harbor, N.Y.). Probes of different lengths and base composition may be used, but preferred embodiments include up to 100 bases, preferably from 12 to 50 bases, and more preferably 18 to 35 bases.

Probes may be labeled with any known detectable label or reporter group, such as a radioisotope, antigen, fluorescent compound, luminescent moiety (chemiluminescent, electrochemiluminescent, or phosphorescent compound), chromophore, enzyme, enzyme cofactor or substrate, dye, hapten, or ligand for detection of the target sequence associated with the probe. Methods of preferentially hybridizing a probe to a target sequence in a sample that may contain other nucleic acids or other biological, organic or inorganic materials, and detecting the signal from the label or reporter group are well known in the art. Preferred embodiments selectively degrade label associated with unhybridized probe and then measure the signal from remaining label associated with hybridized probe. Probes and amplification mixture may include additional sequences that facilitate capture by hybridization with an immobilized oligonucleotide joined to a solid support, by using any known target capture method (See e.g., U.S. Pat. No. 6,110,678), such as used for nucleic acid purification, which may be performed by using an automated system.

In some embodiments, the detection of a target nucleic acid sequence of interest includes the combined use of an isothermal amplification method and a labeled probe such that the product is measured in real time. In another embodiment, the detection of an amplified target nucleic acid sequence of interest includes the transfer of the amplified target nucleic acid to a solid support, such as a membrane, and probing the membrane with a probe, for example a labeled probe, that is complementary to the amplified target nucleic acid sequence. In yet another embodiment, the detection of an amplified target nucleic acid sequence of interest includes the hybridization of a labeled amplified target nucleic acid to probes that are arrayed in a predetermined array with an addressable location and that are complementary to the amplified target nucleic acid.

Real-time amplification monitors the fluorescence emitted during the reaction as an indicator of amplicon production as opposed to the endpoint detection. The real-time progress of the reaction can be viewed in various systems known in the art. Typically, real-time methods involve the detection of a fluorescent reporter, whose signal level or strength increases in direct proportion to the amount of the amplification product in a reaction. By recording the amount of fluorescence emission during the amplicon production, one can monitor the amplification reaction where the first significant increase in the amount of amplified product correlates to the initial amount of target template. The higher the starting copy number of the nucleic acid target, the sooner a significant increase in fluorescence is observed.

In some embodiments, the fluorescently-labeled probes rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a fluorophore and a non-fluorescent quencher on the same probe (for example, using a molecular beacon or a TAQMAN probe) can identify a probe that specifically hybridizes to the DNA sequence of interest and in this way can detect the presence, and/or amount of the target nucleic acid in a sample. In some embodiments, the fluorescently-labeled DNA probes used to identify amplification products have spectrally distinct emission wavelengths, which allow them to be distinguished within the same reaction tube, for example in multiplex reactions. For example, multiplex reactions permit the simultaneous detection of the amplification products of two or more target nucleic acids, such as a control nucleic acid.

The above-described amplification and detection involves hybridization reactions. Hybridization reaction conditions (e.g., temperature, salt concentration, detergents, and other solutes in a reaction mixture), can be selected to allow probes or oligonucleotides used in the amplification and detection to preferentially hybridize to a target nucleic acid sequence and not to non-target nucleic acids in a sample. In conditions of increased stringency (e.g., decreased salt and/or increased temperature), the extent of hybridization decreases as hydrogen bonding between paired bases in a double-stranded hybrid molecule is disrupted, i.e., referred to as "melting." Hybridization conditions affect the stability of double-stranded nucleic acids, i.e., thermal stability of a probe:target hybrid in particular conditions is taken into account in selecting probes specific for a target, e.g., genus-specific or species-specific probe.

A probe's length, sequence, GC content, and thermal stability difference between probe:target hybrids versus probe:non-target hybrids are relevant factors in designing such a probe. To maximize specificity of a probe for its intended target, preferred sequences are designed to hybridize to their targets under high stringency conditions which can be predicted, estimated, or determined by using standard methods known in the art, and preferred conditions are those that maintain hybridization duplex.

Probes (either oligonucleotide probes or circular probes) can be synthesized by using any standard methodology known in the art, e.g., phosphoramidite solid-phase chemistry (Caruthers et al., 1987, Methods in Enzymol. 154:287), automated synthesis using cyanoethyl phosphoramidite (Barone et al., 1984, Nucleic Acids Res. 12 (10):4051), or procedures for synthesizing oligonucleotides containing phosphorothioate linkages (e.g., U.S. Pat. No. 5,449,769), methylphosphonate linkages (e.g., U.S. Pat. No. 5,811,538). Following synthesis, any known method of nucleic acid purification may be used to purify the product.

The probes may be further modified to contain one or more chemical groups to enhance performance or facilitate characterization of amplification products. Examples of such modification include backbone-modified oligonucleotides, or those that include phosphorothioate, methylphosphonate, 2'-O-alkyl, or peptide groups to make the probes resistant to nucleolytic activity of certain polymerases or nucleases, or may include a non-nucleotide linker between nucleotides which do not prevent hybridization and/or elongation of the oligonucleotide (e.g., U.S. Pat. No. 6,031,091). A probe may also contain a mixture of modified and natural bases.

In the above embodiments, the related procedure is broke down to two separate events, such as the initiation of strand displacement in the analyte (FIG. 1) and the detection step of the displaced strand using circular probes (FIG. 2). Each event is broke down to discrete steps, such as nicking, elongation, hybridization of the circular probe, and further nicking and elongation. That detailed description is not intended to be limiting of the invention, but instead is provided to give the reader a better understanding of certain features and details of embodiments of the invention. Given the nature of the events, one skilled in the art would understand that the two events and various steps may occur substantially simultaneously.

In fact, although both events and their respective steps can be carried out as separate reactions and there may be some technical reasons that it may be advantageous to do so for some embodiments, the preferred embodiment would be to perform both events and their respective steps simultaneous in the same reaction setup (e.g. a "single tube" reaction). Thus, one or more embodiments of the methods comprise simply mixing the reagents followed by repeated generation of copies of the target nucleic acid strand and copies of the circular probes using a polymerase and the two CAS9/gRNA complexes that nick the generated double stranded nucleic acid.

In some embodiments, the method of this invention can optionally involve certain pre-amplification steps. For example, sample processing can be performed prior to amplification of a nucleic acid containing a target sequence and may be useful to discriminate a target from non-target nucleic acid present in a sample or to increase assay sensitivity. Sample processing procedures are well known and may include direct or indirect immobilization of nucleic acids from a liquid phase on a support (see e.g., U.S. Pat. Nos. 8,603,743 and 7,189,508). Any suitable support may be used, e.g., matrices or particles, and preferred supports are magnetically charged particles to facilitate automation of the process of recovering a target nucleic acid from other sample components (e.g., U.S. Pat. Nos. 6,110,678, 6,280,952, 6,534,273, and 6,335,166).

Such steps may include separating a nucleic acid template from a crude or processed biological sample before amplification. In that case, additional reagents adapted to these processes can be provided or used together with amplification reagents (e.g., in the same containment vessel or reaction system), or be separate from the amplification reagents.

Methods for isolating a target nucleic acid for use in an isothermal amplification process are well known in the art and may be combined with the isothermal amplification methods described herein. In some embodiments, one or more capture probes can be used in a pre-amplification purification to separate a template nucleic acid from a sample (U.S. Pat. Nos. 6,110,678 and 6,280,952). The pre-amplification separation process may be conducted apart from the isothermal amplification process (e.g., at a different time and/or in a different reaction vessel), or may be part of the isothermal amplification process (e.g., contemporaneous and/or within the same reaction vessel). In other embodiments, a pre-amplification purification method may rely on nonspecific binding of nucleic acids to a support (see e.g., U.S. Pat. Nos. 5,234,809, 6,534,262, and 5,705,628). Any known process to purify a target nucleic acid before the isothermal amplification may be used, although it is not necessary as the method of this invention is robust and specific as described herein.

Uses

The method disclosed herein can be used for detecting various target nucleic acid strands of interest. The strand can be a part of a double stranded nucleic acid or a single-stranded nucleic acid. In some embodiments, the target nucleic acid strand can be one present in a cell of a subject, such as a mammal (e.g., human), a plant, a fungus (e.g., a yeast), a protozoa, a bacterium, or a virus. For example, the target nucleic acid can be present in the genome of an organism of interest (e.g., on a chromosome) or on an extrachromosomal nucleic acid. In some embodiments, the target nucleic acid can be RNA, e.g., an mRNA. In some other embodiments, the target nucleic acid can be DNA (e.g., double-stranded DNA). In particular embodiments, the target nucleic acid can be specific for the organism of interest, i.e., the target nucleic acid is not found in other organisms or not found in organisms similar to the organism of interest.

In some embodiments, the target nucleic acid can be a viral nucleic acid. For example, the viral nucleic acid can be that in human immunodeficiency virus (HIV), an influenza virus (e.g., an influenza A virus, an influenza B virus, or an influenza C virus), or a dengue virus. Exemplary HIV target nucleic acids include sequences found in the Pol region.

The target nucleic acid can be present in a bacterium, e.g., a Gram-positive or a Gram-negative bacterium. Examples of the bacterium include a species of a bacterial genus selected from *Acinetobacter, Aerococcus, Bacteroides, Bordetella, Campylobacter, Clostridium, Corynebacterium, Chlamydia, Citrobacter, Enterobacter, Enterococcus, Escherichia, Helicobacter, Haemophilus, Klebsiella, Legionella, Listeria, Micrococcus, Mobilincus, Moraxella, Mycobacterium, Mycoplasma, Neisseria, Oligella, Pasteurella, Prevotella, Porphyromonas, Pseudomonas, Propionibacterium, Proteus, Salmonella, Serratia, Staphylococcus, Streptococcus, Treponema, Bacillus, Francisella,* or *Yersinia.*

In some embodiments, the target nucleic acid can be a protozoan nucleic acid. For example, the protozoan nucleic acid can be found in *Plasmodium* spp., *Leishmania* spp., *Trypanosoma brucei gambiense, Trypanosoma brucei rhodesiense, Trypanosoma cruzi, Entamoeba* spp., *Toxoplasma* spp., *Trichomonas vaginalis,* and *Giardia duodenalis.*

In some embodiments, the target nucleic acid is a fungal (e.g., yeast) nucleic acid. For example, the fungal nucleic acid can be found in *Candida* spp. (e.g., *Candida albicans*).

In some other embodiments, the target nucleic acid can be a mammalian (e.g., human) nucleic acid. For example, the mammalian nucleic acid can be found in circulating tumor cells, epithelial cells, or fibroblasts. In one example, the target strand is one containing a particular variant, such as single-nucleotide polymorphism (SNP) or a genetic mutation. Examples of such a mutation include a translocation or an inversion.

Compositions

The invention encompasses in vitro, cell-free composition comprising a first complex having a first CAS9 mutant having a single-strand nicking activity and a first gRNA. The composition can further comprise one or more reagents selected from the group consisting of a strand-displacing nucleic acid polymerase, extension nucleotides, a second complex having a second CAS9 mutant having a single-strand nicking activity and a second gRNA, a detecting agent, and a circular probe having (i) a CAS region that is substantially complementary to the second CAS-targeted site and (ii) a tag region. The first gRNA and the second gRNA target a first CAS-targeted site and a second CAS-targeted site of a target nucleic acid strand of interest, respectively, and the first target sequence is different from the second target sequence The detecting agent can be a nucleotide probe, such as a molecular beacon probe or a Yin-Yang probe that is labeled with a fluorophore and a quencher. See e.g., U.S. Pat. Nos. 5,925,517, 6,103,476, 6,150,097, 6,270,967, 6,326,145, and 7,799,522. The composition can also comprise, in addition to the above reagents, one or more of: a salt, e.g., NaCl, $MgCl_2$, KCl, $MgSO_4$; a buffering agent, e.g., a Tris buffer, N-(2-Hydroxyethyl)piperazine-N'-(2-ethanesulfonic acid) (HEPES), 2-(N-Morpholino)ethanesulfonic acid (MES), MES sodium salt, 3-(N-Morpholino)propanesulfonic acid (MOPS), N-tris[Hydroxymethyl]methyl-3-aminopropanesulfonic acid (TAPS); a solubilizing agent; a detergent, e.g., a non-ionic detergent such as Tween-20; a nuclease inhibitor; and the like. For example, in some cases, the composition comprises a buffer for stabilizing the complexes having the CAS9 mutants and gRNA nucleic acids.

Kits

The invention encompasses kits and diagnostic systems for conducting isothermal amplification and/or for detecting a target sequence. To that end, one or more of the reaction components for the methods disclosed herein can be supplied in the form of a kit for use in the detection of a target nucleic acid strand. In such a kit, an appropriate amount of one or more reaction components is provided in one or more containers or held on a substrate (e.g., by electrostatic interactions or covalent bonding).

A kit containing reagents for performing isothermal amplification of a target nucleic acid sequence using the methods described herein may include one or more of the followings: a first CAS9 mutant having a single-strand nicking activity, a first gRNA targeting the first CAS-targeted site, a second CAS9 mutant having a single-strand nicking activity, a second gRNA targeting the second CAS-targeted site, a strand-displacing nucleic acid polymerase, extension nucleotides, one or more circular probes, and detection probes. The kit may also contain additional materials for isothermal amplification, such as one or more of the following components: supports, terminating, modifying or digestion reagents, and osmolytes. The kit may include an apparatus for detecting a detection probe.

The reaction components used in an amplification and/or detection process may be provided in a variety of forms. For example, the components (e.g., enzymes, nucleotide triphosphates, probes and/or primers) can be suspended in an aqueous solution or as a freeze-dried or lyophilized powder, pellet, or bead. In the latter case, the components, when reconstituted, form a complete mixture of components for use in an assay.

A kit or system may contain, in an amount sufficient for at least one assay, any combination of the components described herein, and may further include instructions recorded in a tangible form for use of the components. In some applications, one or more reaction components may be provided in pre-measured single use amounts in individual, typically disposable, tubes or equivalent containers. With such an arrangement, the sample to be tested for the presence of a target nucleic acid can be added to the individual tubes and amplification carried out directly. The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The kits of the invention can comprise any number of additional reagents or substances that are useful for practicing a method of the invention. Such substances include, but are not limited to: reagents (including buffers) for lysis of cells, divalent cation chelating agents or other agents that inhibit unwanted nucleases, control DNA for use in ensuring that the enzyme complexes and other components of reactions are functioning properly, DNA fragmenting reagents (including buffers), amplification reaction reagents (including buffers), and wash solutions. The kits of the invention can be provided at any temperature. For example, for storage of kits containing protein components or complexes thereof in a liquid, it is preferred that they are provided and maintained below 0° C., preferably at or below −20° C., or otherwise in a frozen state.

The container(s) in which the components are supplied can be any conventional container that is capable of holding the supplied form, for instance, microfuge tubes, ampoules, bottles, or integral testing devices, such as fluidic devices, cartridges, lateral flow, or other similar devices. The kits can include either labeled or unlabeled nucleic acid probes for use in detection of target nucleic acids. In some embodiments, the kits can further include instructions to use the components in any of the methods described herein, e.g., a method using a crude matrix without nucleic acid extraction and/or purification. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like).

A system, in addition to containing kit components, may further include instrumentation for conducting an assay, e.g. a luminometer for detecting a signal from a labeled probe and/or a magnetic device for separating nucleic acid hybridized to a capture probe.

Definitions

A "nucleic acid" refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA.

As used herein, the term "target nucleic acid" or "target" refers to a nucleic acid containing a target nucleic acid sequence. A target nucleic acid may be single-stranded or double-stranded, and often is DNA, RNA, a derivative of DNA or RNA, or a combination thereof. A "target nucleic acid sequence," "target sequence" or "target region" means a specific sequence comprising all or part of the sequence of a single-stranded nucleic acid. A target sequence may be within a nucleic acid template, which may be any form of single-stranded or double-stranded nucleic acid. A template may be a purified or isolated nucleic acid, or may be non-purified or non-isolated.

A "target nucleic acid strand" as used herein refers to a strand of a target nucleic acid that is nicked and subject to amplification as disclosed herein. In the case of double-stranded target nucleic acid (e.g., DNA), each strand can be a "target nucleic acid strand" to design crRNA and guide RNAs and practice the method of this invention. The strand of a target nucleic acid that is complementary to and hybridizes with the crRNA and guide RNA is referred to as the "complementary strand" and the strand of the target nucleic acid that is complementary to the "complementary strand" (and is therefore not complementary to the guide RNA) is referred to as the "noncomplementary strand" or "non-complementary strand." One skilled in the art could appreciate that such a "noncomplementary strand" or "non-complementary strand" corresponds to the top strand shown in FIG. 1.

Any target nucleic acid strand of interest can be detected by the method of this invention as long as it (or its complement) has from 5' to 3' two separate targetable sites: a first CAS-targeted site and a second CAS-targeted site. Due to their relative locations, the first CAS-targeted site and the second CAS-targeted site are also referred here as a 5' CAS targeted site and a 3' CAS targeted site, respectively.

A "nucleic acid duplex," "duplex," "nucleic acid hybrid" or "hybrid" refers to a stable nucleic acid structure comprising a double-stranded, hydrogen-bonded region, e.g., RNA:RNA, RNA:DNA and DNA:DNA duplex molecules and analogs thereof. Such structure may be detected by any known means, e.g., by using a labeled probe, an optically active probe-coated substrate sensitive to changes in mass at its surface (U.S. Pat. No. 6,060,237), or binding agents (U.S. Pat. No. 5,994,056).

"Nuclease" and "endonuclease" are used interchangeably herein to mean an enzyme which possesses catalytic activity for DNA cleavage. By "cleavage" it is meant the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guide RNA and a CAS9 variant is used for targeted single-stranded DNA cleavage, i.e., nicking.

By "cleavage domain" or "active domain" or "nuclease domain" of a nuclease it is meant the polypeptide sequence or domain within the nuclease which possesses the catalytic activity for DNA cleavage. A cleavage domain can be contained in a single polypeptide chain or cleavage activity can result from the association of two (or more) polypeptides. A single nuclease domain may consist of more than one isolated stretch of amino acids within a given polypeptide.

A "CAS9 mutant" or "CAS9 variant" refers to an isolated protein or polypeptide derivative of the wild type *S. pyogenes* CAS9 protein (i.e., SEQ ID NO: 1), e.g., an isolated protein having one or more point mutations, insertions, deletions, truncations, a fusion protein, or a combination thereof. It retains substantially the nuclease activity of the CAS9 protein. The isolated protein or polypeptide can comprise, consist of, or consist essentially of the sequence of SEQ ID NO: 2 or 3 or a fragment thereof. In general, the mutant/variant is at least 75% (i.e., any number between 75% and 100%, inclusive, e.g., 80%, 85%, 90%, 95%, 96%, 97%, 98%, 99%, and 100%) identical to SEQ ID NO: 1, 2, or 3. Like the wild type CAS9 protein, the mutant/variant contains one or more functional cleavage domains and active domains or nuclease domains of a nuclease and can bind to an RNA molecule and be targeted to a specific DNA sequence via the RNA molecule. Examples of these domains include RuvC like motifs (aa. 7-22, 759-766 and 982-989 in SEQ ID NO: 1) and HNH motif (aa 837-863). See Gasiunas et al., Proc Natl Acad Sci USA. 2012 Sep. 25; 109(39): E2579-E2586 and WO2013176772. The RNA molecule comprises a sequence that is complementary to a complementary strand within a target DNA, thus targeting the bound polypeptide to a specific location within the target DNA (the target sequence).

A nuclease or a nuclease mutant/variant (e.g., a CAS9 mutant/variant) "having a single-strand nicking activity" refers to a nuclease or a nuclease mutant/variant that has reduced ability to cleave one of two strands of a dsDNA as compared to that to cleave the other strand. For example, the nuclease or a nuclease mutant/variant can have a mutation (e.g., amino acid substitution) that reduces the function of the RuvC domain (or the HNH domain) and as a result reduces the ability to cleave the non-complementary strand (or the complementary strand) of the target DNA. Examples of such variant include the D10A and H839 CAS9 variants described above and CAS enzymes for other species with the same substitution at equivalent site of D10 or H839 of SEQ ID NO: 1).

As used herein, the term "guide RNA" (also referred to herein as "DNA-targeting RNA") refers to a RNA molecule or a group of RNA molecules that can bind to a nuclease (such as CAS9 or its nuclease variant) and target the nuclease to a specific location within a target DNA. A guide RNA comprises two segments, a "DNA-targeting segment" and a "protein-binding segment." These two segments can be on the same RNA molecule or on two or more separate RNA molecules. The DNA-targeting segment comprises a nucleotide sequence that is complementary to a specific sequence within a strand of a target DNA (i.e., the complementary strand of the target DNA). The protein-binding segment interacts with a nuclease, such as a CAS9 or CAS9 related polypeptide. As mentioned above, in the case of CAS9, site-specific cleavage of the target DNA occurs at locations determined by both (i) base-pairing complementarity between the DNA-targeting segment and the target DNA; and (ii) a short motif referred to as the PAM sequence in the target DNA. Guide RNAs may include modified bases or backbone.

As used herein the term "amplification" and its variants includes any process for producing multiple copies or complements of at least some portion of a polynucleotide, said polynucleotide typically being referred to as a "template." The template polynucleotide can be single stranded or double stranded. Amplification of a given template can result in the generation of a population of polynucleotide amplification products, collectively referred to as an "amplicon." The polynucleotides of the amplicon can be single stranded or double stranded, or a mixture of both. Typically, the template will include a target sequence, and the resulting amplicon will include polynucleotides having a sequence that is either substantially identical or substantially complementary to the target sequence. In some embodiments, the polynucleotides of a particular amplicon are substantially identical, or substantially complementary, to each other; alternatively, in some embodiments the polynucleotides within a given amplicon can have nucleotide sequences that vary from each other. Amplification can proceed in linear or exponential fashion, and can involve repeated and consecutive replications of a given template to form two or more amplification products. Some typical amplification reactions involve successive and repeated cycles of template-based nucleic acid synthesis, resulting in the formation of a plurality of daughter polynucleotides containing at least some portion of the nucleotide sequence of the template and sharing at least some degree of nucleotide sequence identity (or complementarity) with the template. In some embodiments, each instance of nucleic acid synthesis, which can be referred to as a "cycle" of amplification, includes creating free 3' end (e.g., by nicking one strand of a dsDNA) thereby generating a primer and primer extension steps; optionally, an additional denaturation step can also be included wherein the template is partially or completely denatured. In some embodiments, one round of amplification includes a given number of repetitions of a single cycle of amplification. For example, a round of amplification can include 5, 10, 15, 20, 25, 30, 35, 40, 50, 75, 100 or more repetitions of a particular cycle. In one exemplary embodiment, amplification includes any reaction wherein a particular polynucleotide template is subjected to two consecutive cycles of nucleic acid synthesis. The synthesis can include template-dependent nucleic acid synthesis. As disclosed herein, amplification of this invention includes isothermal amplification.

As used herein, the term "isothermal" means conducting a reaction at substantially constant temperature, i.e., without varying the reaction temperature in which a nucleic acid polymerization reaction occurs. Isothermal temperatures for isothermal amplification reactions depend on the strand-displacing nucleic acid polymerase used in the reactions. Generally, the isothermal temperatures are below the melting temperature (Tm; the temperature at which half of the potentially double-stranded molecules in a mixture are in a single-stranded, denatured state) of the predominant reaction product, i.e., generally 90° C. or below, usually between about 20° C. and 75° C., and preferably between about 30° C. and 60° C., or more preferably at about 37° C.

The term "primer" or "primer oligonucleotide" refers to a strand of nucleic acid or an oligonucleotide capable of hybridizing to a template nucleic acid and acting as the initiation point for incorporating extension nucleotides according to the composition of the template nucleic acid for nucleic acid synthesis. "Extension nucleotides" refer to any nucleotide capable of being incorporated into an extension product during amplification, i.e., DNA, RNA, or a derivative if DNA or RNA, which may include a label.

The term "detection probe" refers to an oligonucleotide having a sequence sufficiently complementary to its target sequence to form a probe:target hybrid stable for detection under stringent hybridization conditions. A probe is typically a synthetic oligomer that may include bases complementary to sequence outside of the targeted region which do not prevent hybridization under stringent hybridization conditions to the target nucleic acid. A sequence non-complementary to the target may be a homopolymer tract (e.g., poly-A or poly-T), promoter sequence, restriction endonuclease recognition sequence, or sequence to confer desired secondary or tertiary structure (e.g., a catalytic site or hairpin structure), or a tag region which may facilitate detection and/or amplification. "Stable" or "stable for detection" means that the temperature of a reaction mixture is at least 2° C. below the melting temperature (Tm) of a nucleic acid duplex contained in the mixture, more preferably at least 5° C. below the Tm, and even more preferably at least 10° C. below the Tm.

As used herein, a "tag" refers to a non-target nucleic acid component (generally DNA) that provides a means of addressing a nucleic acid fragment to which it is joined. For example, in preferred embodiments, a tag comprises a nucleotide sequence that permits identification, recognition, and/or molecular or biochemical manipulation of the DNA to which the tag is attached (e.g., by providing a site for annealing an oligonucleotide, such as a primer for extension by a DNA polymerase, or an oligonucleotide for capture or for a ligation reaction). The process of joining the tag to the DNA molecule is sometimes referred to herein as "tagging" and DNA that undergoes tagging or that contains a tag is referred to as "tagged" (e.g., "tagged DNA"). A "tag portion" or a "tag domain" or "tag region" means a portion or domain of a tag that exhibits a sequence for a desired intended purpose or application. A region or sequence that is recognizable by a detecting agent means that the region or sequence can be recognized by such as a detecting agent (e.g., hybridized to a detection probe).

"Hybridization" or "hybridize" or "anneal" refers to the ability of completely or partially complementary nucleic acid strands to come together under specified hybridization conditions in a parallel or preferably antiparallel orientation to form a stable double-stranded structure or region (sometimes called a "hybrid") in which the two constituent strands are joined by hydrogen bonds. Although hydrogen bonds typically form between adenine and thymine or uracil (A and T or U) or cytosine and guanine (C and G), other base pairs may form (e.g., Adams et al., The Biochemistry of the Nucleic Acids, 11th ed., 1992).

"Preferentially hybridize" means that under stringent hybridization conditions, probes can hybridize to their target nucleic acid sequence to form stable hybrids, e.g., to indicate the presence of at least one sequence or organism of interest in a sample. A probe hybridizes to its target nucleic acid specifically, i.e., to a sufficiently greater extent than to a non-target nucleic acid to accurately detect the presence (or absence) of the intended target sequence. Preferential hybridization generally refers to at least a 10-fold difference between target and non-target hybridization signals in a sample.

The term "stringent hybridization conditions" or "stringent conditions" means conditions in which a probe or oligomer hybridizes specifically to its intended target nucleic acid sequence and not to another sequence. Stringent conditions may vary depending well-known factors, e.g., GC content and sequence length, and may be predicted or determined empirically using standard methods well known to one of ordinary skill in molecular biology (e.g., Sambrook, J. et al., 1989, Molecular Cloning, A Laboratory Manual, 2nd ed., Ch. 11, pp. 11.47-11.57, (Cold Spring Harbor Laboratory Press, Cold Spring Harbor, N.Y.)).

"Substantially homologous" or "substantially corresponding" means a probe, nucleic acid, or oligonucleotide has a sequence of at least 10, 20, 30, 40, 50, 100, 150, 200, 300, 400, or 500 contiguous bases that is at least 80% (preferably at least 85%, 90%, 95%, 96%, 97%, 98%, and 99%, and most preferably 100%) identical to contiguous bases of the same length in a reference sequence. Homology between sequences may be expressed as the number of base mismatches in each set of at least 10 contiguous bases being compared.

"Substantially complementary" means that an oligonucleotide has a sequence containing at least 10, 20, 30, 40, 50, 100, 150, 200, 300, 400, or 500 contiguous bases that are at least 80% (preferably at least 85%, 90%, 95%, 96%, 97%, 98%, and 99%, and most preferably 100%) complementary to contiguous bases of the same length in a target nucleic acid sequence. Complementarity between sequences may be expressed a number of base mismatches in each set of at least 10 contiguous bases being compared.

The term "isolate" or "isolating" target nucleic acid means that a portion of the target nucleic acid in a sample is concentrated within or on a reaction receptacle, device, or carrier (e.g., tube, cuvette, microtiter plate well, filter, membrane, slide, pipette tip) in a fixed or releasable manner to purify the target from other components. "Purify" or "purifying" means that one or more components of a sample are removed from other sample components. Purified components may include particles (e.g., virus) but preferably are target nucleic acids in a generally aqueous solution phase which may include other materials, e.g., proteins, carbohydrates, lipids, non-target nucleic acid and/or labeled probes. Purifying separates a target nucleic acid from about 70%, more preferably about 90% and, even more preferably, about 95% of the other sample components.

An "isolated polypeptide" or "isolated protein" refers to a polypeptide or protein that has been separated from other proteins, lipids, and nucleic acids with which it is naturally associated. The polypeptide can constitute at least 10% (i.e., any percentage between 10% and 100%) by dry weight of the purified preparation.

The "percent identity" of two amino acid sequences or of two nucleic acids is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

As used herein, the term "subject" refers to any organism having a genome, preferably, a living animal, e.g., a mammal, which has been the object of diagnosis, treatment, observation or experiment. Examples of a subject can be a human, a livestock animal (beef and dairy cattle, sheep, poultry, swine, etc.), or a companion animal (dogs, cats, horses, etc).

The term "biological sample" refers to a sample obtained from an organism (e.g., patient) or from components (e.g., cells) of an organism. The sample may be of any biological tissue, cell(s) or fluid. The sample may be a "clinical sample" which is a sample derived from a subject, such as a human patient or veterinary subject. Such samples include, but are not limited to, saliva, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample." A biological sample may also include a substantially purified or isolated protein, membrane preparation, or cell culture.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

The term "mixture" as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of surface-bound oligonucleotides, as is commonly known in the art and described below, is not a mixture of surface-bound oligonucleotides because the species of surface-bound oligonucleotides are spatially distinct and the array is addressable.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 20" may indicate a range of 18 to 22, and "about 1" may mean from 0.9-1.1. Other meanings of "about" may be apparent from the context, such as rounding off, so, for example "about 1" may also mean from 0.5 to 1.4.

Preferred embodiments are illustrated herein, but those skilled in the art will appreciate that other components and conditions in addition to those illustrated may be used in the methods described herein.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. An isothermal method for detecting in a sample a target nucleic acid strand having (i) a first CAS-targeted site having a first target sequence and a first PAM site which is 3' to the first target sequence, and (ii) a second CAS-targeted site having a second target sequence and a second PAM site which is 3' to the second target sequence, the first target sequence being different and upstream from the second target sequence, the method comprising the steps of:

(a) contacting a sample suspected to contain the target nucleic acid strand with:
        a first CAS9 mutant having a single-strand nicking activity,
        a first guide RNA (gRNA) targeting the first CAS-targeted site,
        a strand-displacing nucleic acid polymerase, and nucleotides,
    under conditions allowing
        nicking of the target nucleic acid strand by the CAS9 mutant at the first CAS targeted site, and
        strand-displacing by the strand-displacing nucleic acid polymerase to create one or more copies of a section of the target nucleic acid strand, each copy containing the second CAS-targeted site;
    (b) contacting said one or more copies with:
        a second CAS9 mutant having a single-strand nicking activity,
        a second gRNA targeting the second CAS-targeted site,
        a strand-displacing nucleic acid polymerase,
        nucleotides, and
        one or more circular probes, each having a tag region and a CAS region that is complementary to the second CAS-targeted site,
    under conditions allowing
        hybridizing of said one or more copies to said one or more circular probes to generate one or more annealed copies,
        nicking of said one or more annealed copies by the second CAS9 mutant at the second CAS-targeted site, and
        strand-displacing by the strand-displacing nucleic acid polymerase to create one or more extension products of said one or more annealed copies, each product containing a detecting region that is complementary to the tag region and recognizable by a detecting agent; and
    (c) detecting presence of the one or more extension products using the detecting agent, whereby the presence of the one or more extension products is an indicator of the presence of the target nucleic acid strand in the sample.

2. The method of claim 1, wherein steps (a) and (b) are carried out by incubating a reaction mixture containing
    (i) the sample,
    (ii) the first CAS9 mutant,
    (iii) the first gRNA,
    (iv) the second CAS9 mutant,
    (v) the second gRNA,
    (vi) the strand-displacing nucleic acid polymerase,
    (vii) the nucleotides, and
    (viii) the one or more circular probes
under conditions permitting:
    (i) nicking the target nucleic acid strand by the first CAS9 mutant at the first CAS targeted site,
    (ii) strand displacing by the strand-displacing nucleic acid polymerase to create said one or more copies,
    (iii) hybridizing said one or more copies to said one or more circular probes to generate said one or more annealed copies,
    (iv) nicking said one or more annealed copies by the second CAS9 mutant at the second CAS-targeted site, and
    (v) strand displacing by the strand-displacing nucleic acid polymerase to create said one or more extension products.

3. The method of claim 1, wherein the first or second CAS9 mutant is a DI OA or H839A mutant version of SEQ ID NO.: 1.

4. The method of claim 1, wherein the strand-displacing nucleic acid polymerase is a φ29 DNA polymerase.

5. The method of claim 1, wherein the detecting agent is a nucleotide probe.

6. The method of claim 5, wherein the nucleotide probe is a molecular beacon probe or a Yin-Yang probe that is labeled with a fluorophore and a quencher.

7. The method of claim 6, wherein detecting step is carried out by measuring the fluorescent signal emitted upon hybridization of the nucleotide probe to the detecting region.

8. The method of claim 1, wherein said one or more copies contain the first PAM site, or said one or more extension products contain the second CAS-targeted site.

9. The method of claim 1, wherein the target nucleic acid strand is on one strand of a genomic DNA of a microorganism or a cell of a subject.

10. The method of claim 9, wherein the sample contains the microorganism or a cell of the subject and the method further comprises lysing the microorganism or the cell before step (a) or (b).

11. The method of claim 8, wherein the target nucleic acid strand contains a mutation of the subject.

12. The method of claim 11, wherein the mutation is a translocation or an inversion.

13. The method of claim 9, wherein the subject is an animal.

14. The method of claim 13, wherein the animal is a human.

15. The method of claim 9, wherein the microorganism is selected from the group consisting of a virus, a bacterium, and a fungus.

16. The method of claim 9, wherein the microorganism is a pathogen.

* * * * *

UNITED STATES PATENT AND TRADEMARK OFFICE
CERTIFICATE OF CORRECTION

| | | |
|---|---|---|
| PATENT NO. | : 9,850,525 B2 | Page 1 of 2 |
| APPLICATION NO. | : 14/607781 | |
| DATED | : December 26, 2017 | |
| INVENTOR(S) | : Carsten-Peter Carstens | |

It is certified that error appears in the above-identified patent and that said Letters Patent is hereby corrected as shown below:

On the Title Page

Item (56), in Column 2, under "Other Publications", Line 4, delete "RNAguided" and insert -- RNA guided --, therefor.

On the page 2, in Column 1, under "Other Publications", Line 1, delete "CRISPRCas9" and insert -- CRISPR Cas9 --, therefor.

In the Specification

In Column 3, Line 9, after "agent" insert -- . --.

In Column 5, Line 25, delete "520030082590," and insert -- US20030082590, --, therefor.

In Column 5, Line 66, delete "Wastson-Crick" and insert -- Watson-Crick --, therefor.

In Column 6, Line 12, delete "S. thermophiles" and insert -- S. thermophilus --, therefor.

In Column 10, Line 31, delete "CRSIPR" and insert -- CRISPR --, therefor.

In Column 10, Line 34, delete "CRSIPR" and insert -- CRISPR --, therefor.

In Column 10, Line 39, delete "CRSIPR" and insert -- CRISPR --, therefor.

In Column 15, Line 10, delete "5'→3" and insert -- 5'→3' --, therefor.

In Column 20, Line 19, delete "Mobilincus," and insert -- Mobiluncus, --, therefor.

In Column 20, Line 56, after "sequence" insert -- . --.

Signed and Sealed this
Fifth Day of June, 2018

Andrei Iancu
*Director of the United States Patent and Trademark Office*

CERTIFICATE OF CORRECTION (continued)
U.S. Pat. No. 9,850,525 B2

In the Claims

In Column 50, Line 46, in Claim 3, delete "DI OA" and insert -- D10A --, therefor.